(12) United States Patent
Ying et al.

(10) Patent No.: US 10,717,798 B2
(45) Date of Patent: Jul. 21, 2020

(54) POLYMERIC COMPOSITION

(71) Applicant: AGENCY FOR SCIENCE, TECHNOLOGY AND RESEARCH, Singapore (SG)

(72) Inventors: Jackie Y. Ying, Singapore (SG); Nandanan Erathodiyil, Singapore (SG); Hong Wu, Singapore (SG); Hsi-Min Chan, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 98 days.

(21) Appl. No.: 15/779,513

(22) PCT Filed: Nov. 22, 2016

(86) PCT No.: PCT/SG2016/050575
§ 371 (c)(1),
(2) Date: May 25, 2018

(87) PCT Pub. No.: WO2017/091150
PCT Pub. Date: Jun. 1, 2017

(65) Prior Publication Data
US 2018/0346626 A1    Dec. 6, 2018

(30) Foreign Application Priority Data

Nov. 26, 2015   (SG) ............................ 10201509758W

(51) Int. Cl.
*C08K 5/09* (2006.01)
*C08F 220/18* (2006.01)
(Continued)

(52) U.S. Cl.
CPC ............ *C08F 220/18* (2013.01); *A61L 27/34* (2013.01); *A61L 27/52* (2013.01); *C08F 220/54* (2013.01);
(Continued)

(58) Field of Classification Search
CPC ...................................................... C08K 5/09
See application file for complete search history.

(56) References Cited

U.S. PATENT DOCUMENTS 8,709,452 B2   4/2014   Varghese et al.
2012/0157602 A1   6/2012   Chou

FOREIGN PATENT DOCUMENTS

CN   104892949 A   9/2015
TW   201122003 A1   7/2011

OTHER PUBLICATIONS

Romanski, J.; Karbarz, M.; Pyrzynska, K.; Jurczak, J.; Stojek, Z. J. Polym. Sci. Part A: Polym. Chem. 2012, 50, 542-550. Wiley Periodicals, Inc. (Year: 2012).*

(Continued)

*Primary Examiner* — Michael F Pepitone
(74) *Attorney, Agent, or Firm* — Womble Bond Dickinson (US) LLP

(57) ABSTRACT

A polymeric composition comprising (i) a plurality of monomers selected from (a) a carboxylic acryloyi monomer; (b) a sulfonic acryloyi monomer; (c) an amine acryloyi monomer; (d) a hydroxyl acryloyi monomer; (e) an alkyl acryloyi monomer; and (f) a polyalkylene hydroxyl acryloyi monomer; (ii) a divalent metallic crosslinking agent; and (c) a stabilizing agent is disclosed herein. Also provided are the use of said polymeric composition as a hydrogel coating material, a method of synthesizing the polymeric composition and the use of the hydrogel material.

20 Claims, 11 Drawing Sheets

| Hydrogel | A | B | C | D | E | F | G | H | I | J |
|---|---|---|---|---|---|---|---|---|---|---|
| MLL Concentration (%) | 0 | 2.5 | 5 | 10 | 20 | 25 | 30 | 50 | 75 | 100 |

| (51) | Int. Cl. | |
|---|---|---|
| | A61L 27/52 | (2006.01) |
| | A61L 27/34 | (2006.01) |
| | C08L 33/08 | (2006.01) |
| | C08F 220/54 | (2006.01) |
| | C09D 5/16 | (2006.01) |
| | C08F 220/60 | (2006.01) |
| | C08K 3/014 | (2018.01) |
| | C09D 7/40 | (2018.01) |
| | C08F 220/58 | (2006.01) |
| | C08K 13/02 | (2006.01) |
| | C08K 5/00 | (2006.01) |
| | C08L 33/24 | (2006.01) |

(52) U.S. Cl.
CPC .......... *C08F 220/58* (2013.01); *C08F 220/60* (2013.01); *C08K 3/014* (2018.01); *C08K 5/005* (2013.01); *C08K 5/09* (2013.01); *C08K 13/02* (2013.01); *C08L 33/08* (2013.01); *C08L 33/24* (2013.01); *C09D 5/1606* (2013.01); *C09D 5/1637* (2013.01); *C09D 7/40* (2018.01); *C08L 2203/02* (2013.01)

(56) References Cited

OTHER PUBLICATIONS

The Extended European Search Report for PCT Application No. PCT/SG2016050575 dated Jul. 15, 2019, 19 pages.
IP Office of Singapore—Notification of Transmittal of the International Search Report & the Written Opinion of the International Searching Authority, or the Declaration, with a copy of the ISR & Written Opinion dated Feb. 14, 2017 for Int'l. Application No. PCT/SG2016/050575 (13 pgs).
IP Office of Singapore—Int'l. Preliminary Report on Patentability dated Feb. 19, 2018 with Chapter II Demand with Article 34 Amendment submitted Sep. 25, 2017 for International Application No. PCT/SG2016/050575 (19 pgs).
Campbell, D., et al., "Zwitterionic and Charge-Balanced Polyampholyte Copolymer Hydrogels." *Advanced Materials Research*, Aug. 31, 2008, vol. 55-57, pp. 729-732.
Chen, S., et al., "Surface Hydration: Principles and applications toward low-fouling/nonfouling biomaterials." *Polymer*, Aug. 18, 2010, vol. 51, No. 23, pp. 5283-5293.
Das, M., et al., "Preparation, characterization, and water sorption study of 2-acrylamido-2-methylpropane sulfonic acid (AMPS) based hyrdrogel." *Journal of Chemical and Pharmaceutical Research*, Oct. 31, 2014, vol. 6, No. 10, pp. 800-806.
Gan, T., et al., "In Situ Gelation of P(NIPAM-HEMA) Microgel Dispersion and Its Applications as Injectable 3D Cell Scaffold." *Biomacromolecules*, Apr. 14, 2009, vol. 10, No. 6, pp. 1410-1415.
Mackiewicz, M., et al., "New ampholytic microgels based on N-isopropylacrylamide and α-amino acid: changes in swelling behavior as a function of temperature pH and divalent cation concentration." *RSC Advances*, Sep. 22, 2014, vol. 4, No. 90, pp. 48905-48911.
San Miguel, V., et al., "Self-Assembly of Physical Crosslinked Micelles of Poly(2-acrylamido-2-methyl-1-propane sulphonic acid-co-isodecyl methacrylate)-copper(II) complexes." *European Polymer Journal*, Feb. 20, 2008, vol. 44, No. 5, pp. 1368-1377.
Varghese, S., et al., "Role of Hyrophobicity on Structure of Polymer-Metal Complexes." *J. Phys. Chem. B.*, May 19, 2001, vol. 105, No. 23, pp. 5368-5373.

* cited by examiner

[Fig. 1]
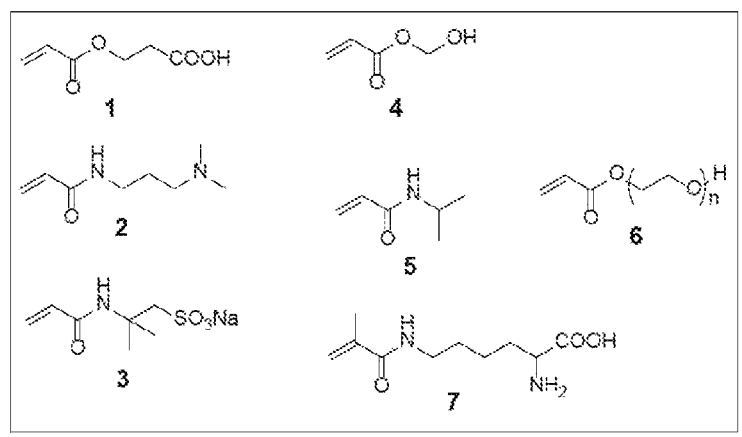
| Hydrogel | A | B | C | D | E | F | G | H | I | J |
|---|---|---|---|---|---|---|---|---|---|---|
| MLL Concentration (%) | 0 | 2.5 | 5 | 10 | 20 | 25 | 30 | 50 | 75 | 100 |

[Fig. 2]
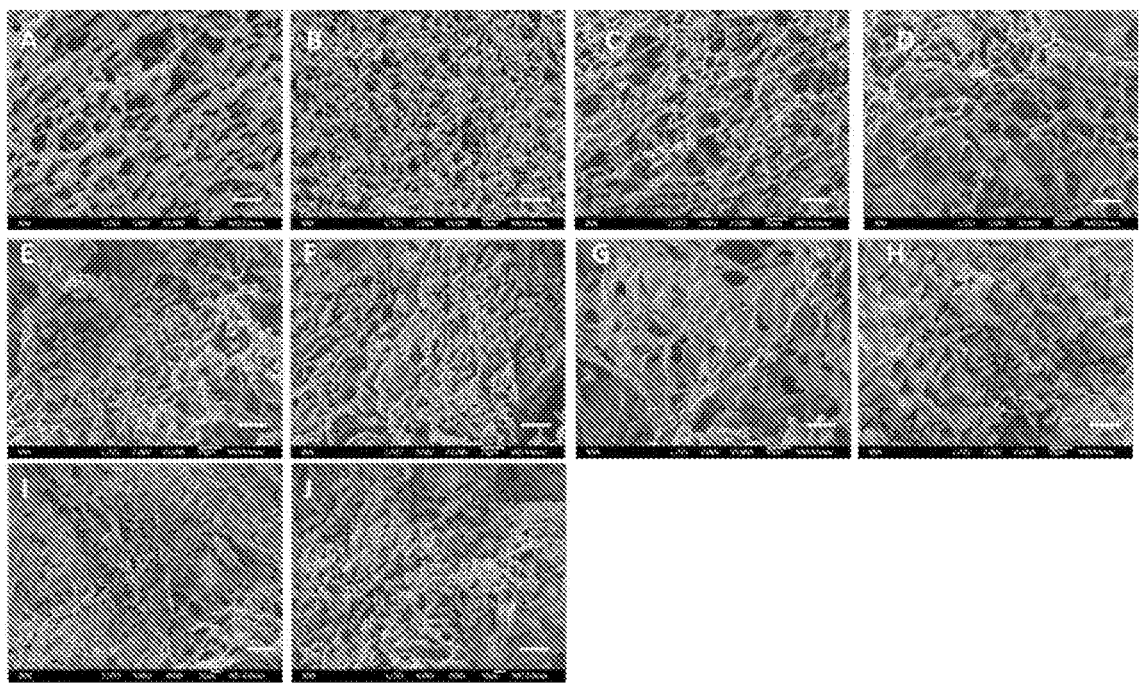

[Fig. 3]
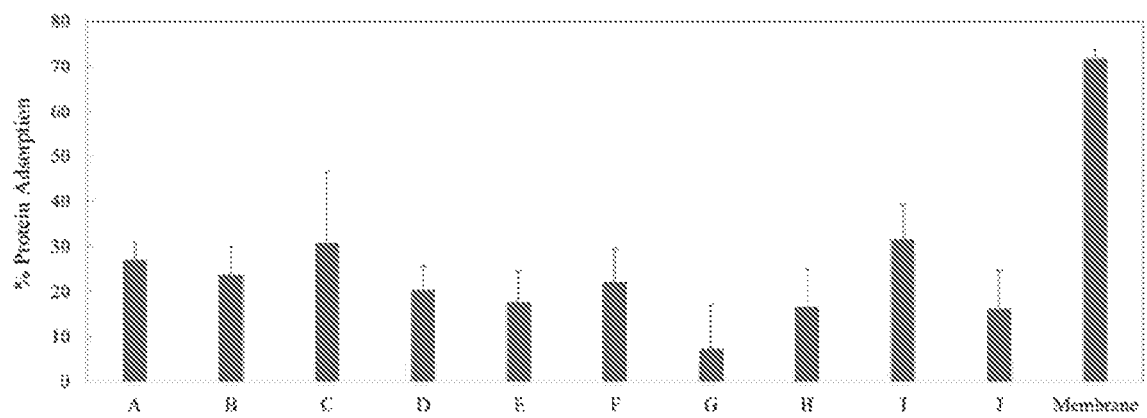

[Fig. 4]
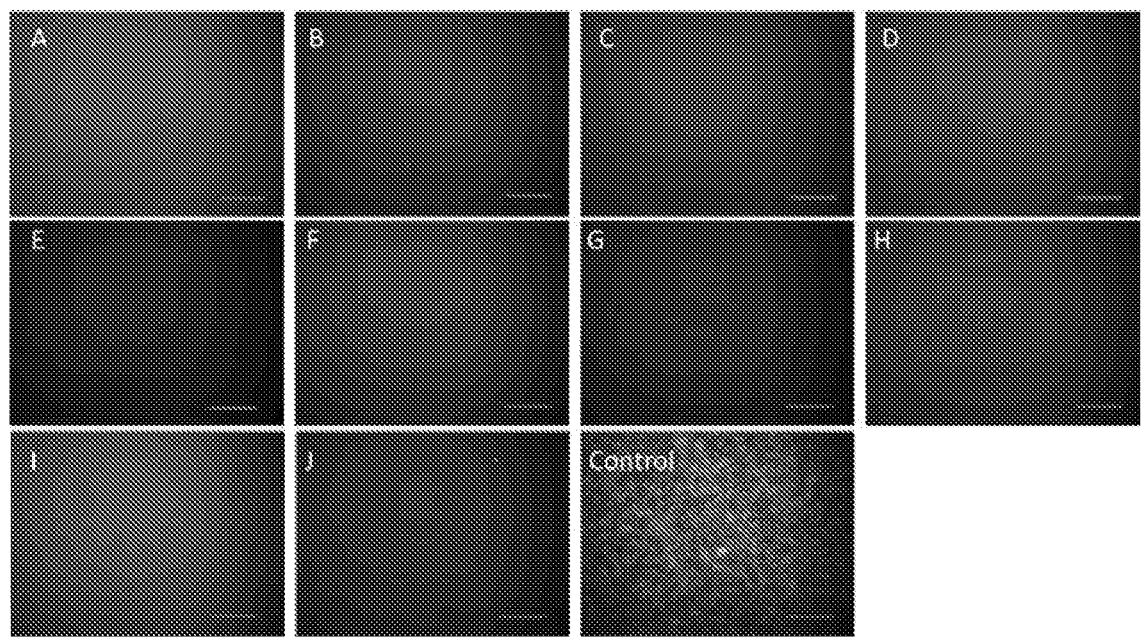

[Fig. 5]
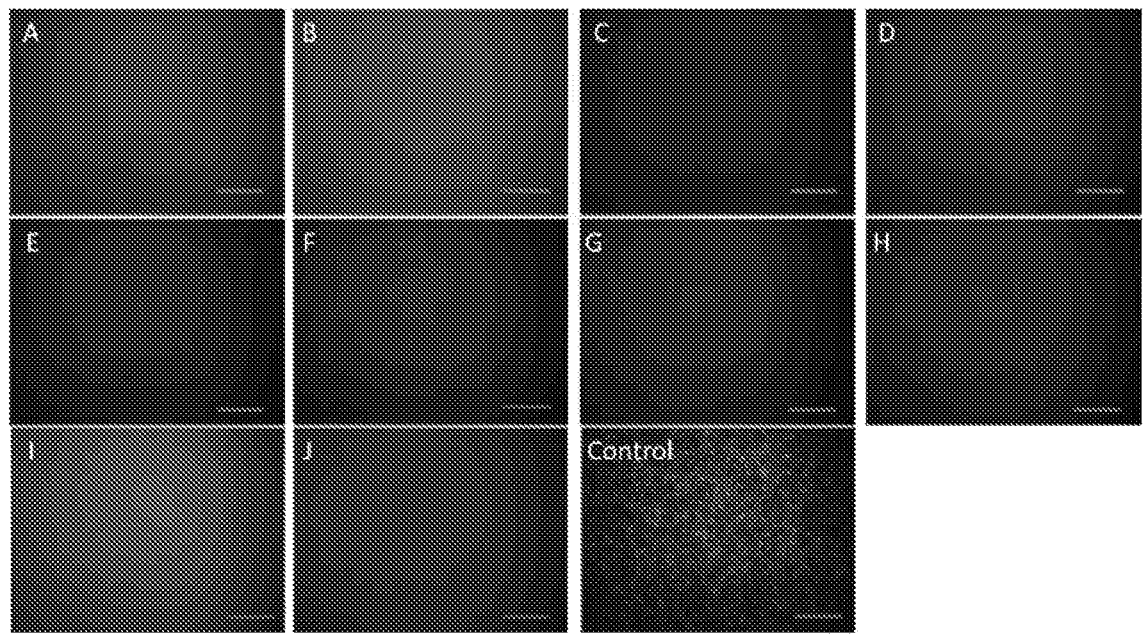

[Fig. 6]
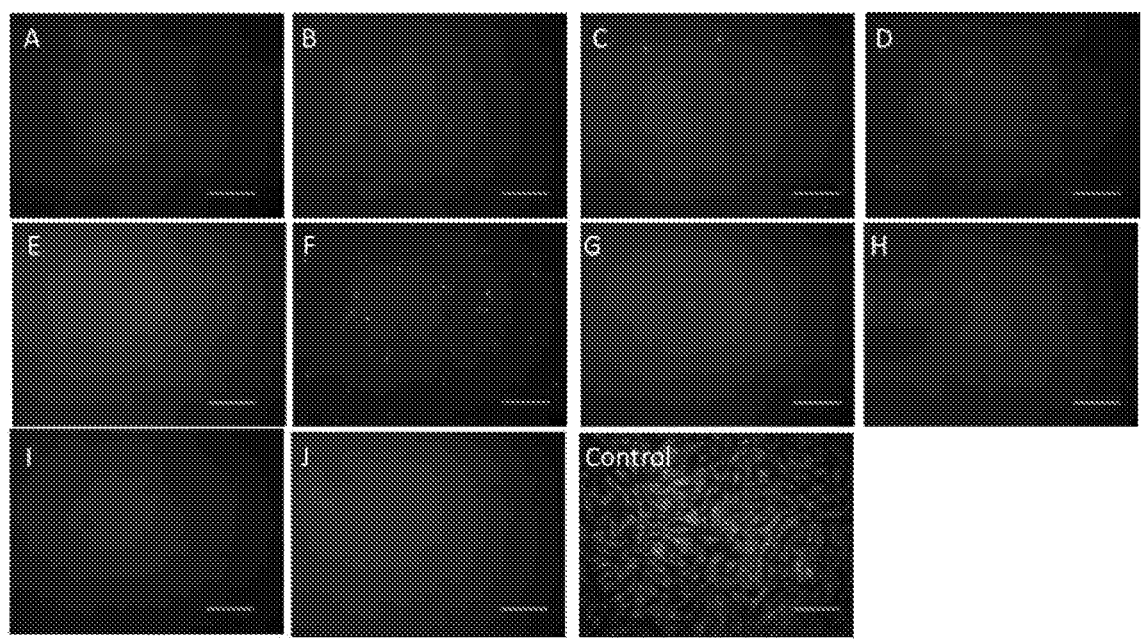

[Fig. 7]
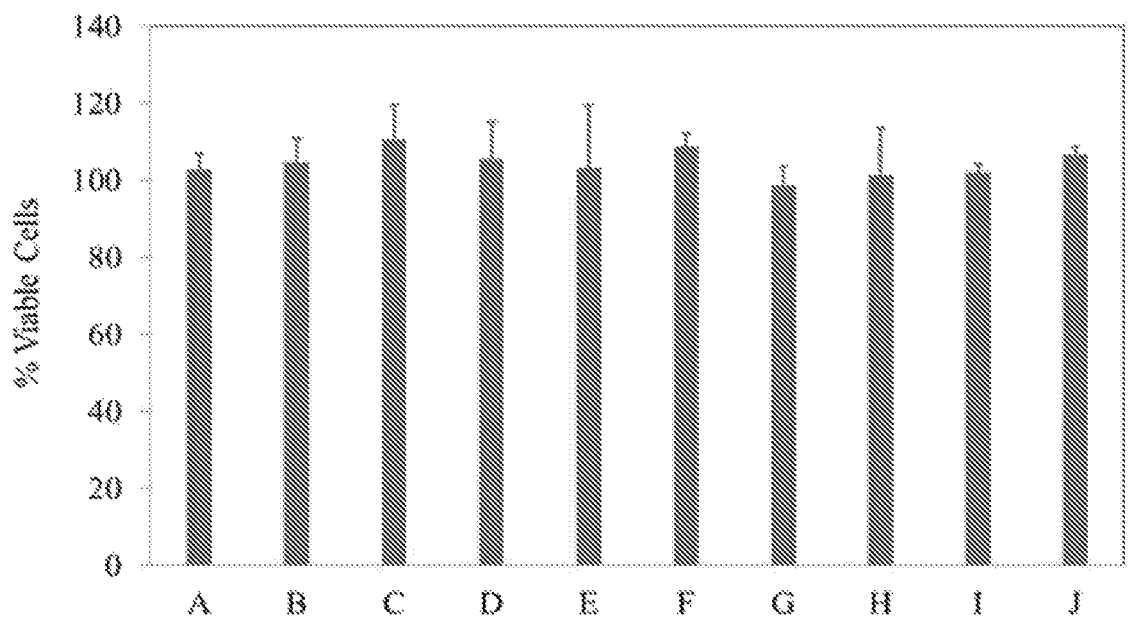

[Fig. 8]
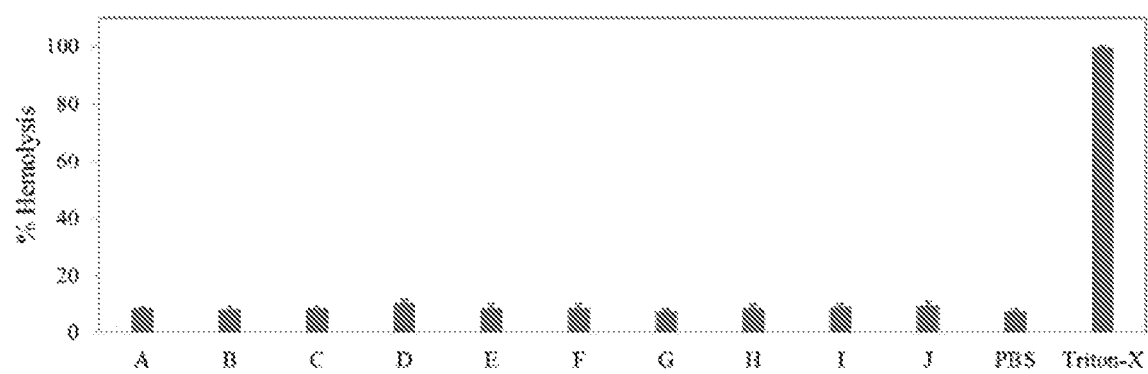

[Fig. 9]
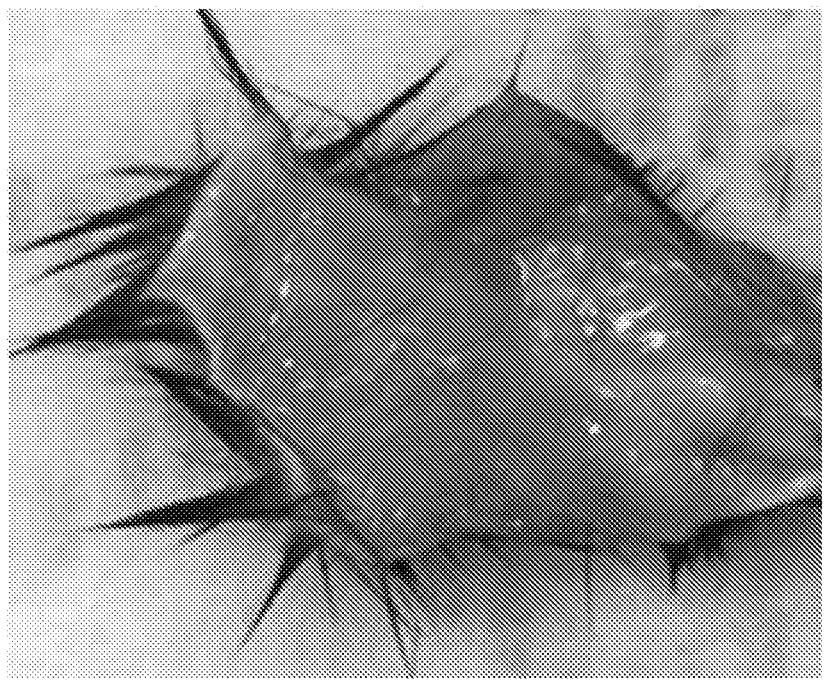

[Fig. 10]
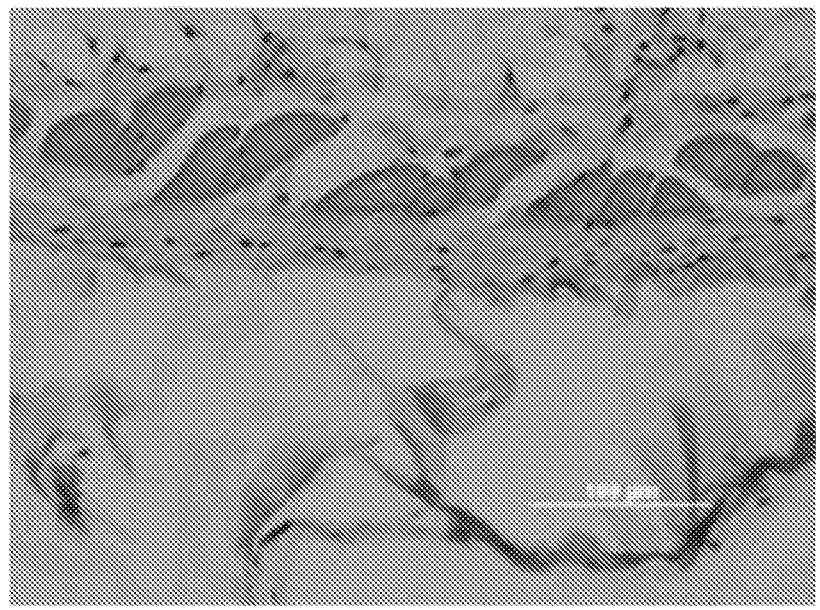

[Fig. 11]
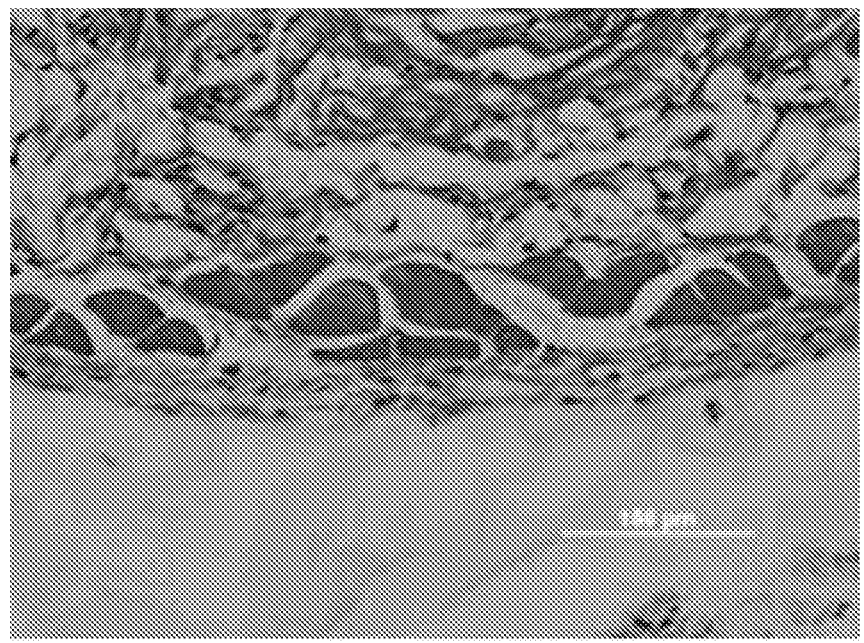

POLYMERIC COMPOSITION

CROSS-REFERENCE TO RELATED APPLICATIONS

This patent application is a U.S. National Phase application under 35 U.S.C. § 371 of International Application No. PCT/SG2016/050575, filed 22 Nov. 2016, entitled A POLYMERIC COMPOSITION, which claims priority to Singapore Patent Application No. 10201509758W, filed 26 Nov. 2015.

TECHNICAL FIELD

The present invention generally relates to a polymeric composition. The present invention also relates to a polymeric composition as a hydrogel coating material, a method of synthesizing the polymeric composition and to uses thereof.

BACKGROUND ART

The development of technology in the twentieth century allows biomedical devices to be used widely in many different parts of the body for applications such as orthopaedic implants, pacemakers, cardiovascular stents, neural prosthetics and drug delivery systems. For example, between 1990 and 2000, the number of total hip replacements operation increased by 33%; this number is estimated to increase by up to 50% between 2000 and 2030. Over the past two decades, coronary stents have become a new standard in angioplasty procedure. Sustained intraocular drug release with implantable devices has been used to treat vitreoretinal diseases. Often, complications arise from these biomedical devices due to inflammation and/or foreign body reaction. Inflammation is caused by the implant's inability to resist bacteria adhesion. Foreign body reaction occurs when the implant is encapsulated with a dense collagen capsule. Direct medical costs associated with bacterial infections exceed $3 billion annually in the U.S. alone. To minimize bacteria adhesion and foreign body reaction, an anti-fouling material is often coated onto biomedical devices before their implantation.

Polyethylene glycol (PEG) and poly (2-hydroxyethyl methacrylate) (PHEMA) hydrogel are commonly used anti-fouling material in contact lenses, tissue scaffolds, drug delivery carriers and medical implants. Despite the low cost of PEG, long-term application of PEG may cause the device to oxidize, eventually destroying its hydrophilic properties and limiting long-term in vivo application. PHEMA only partially reduces non-specific protein adsorption. Other existing anti-fouling materials give rise to foreign body reactions. Therefore, it is important to develop a novel anti-fouling material that would tackle these problems.

Zwitterionic polymers are polyampholytes bearing equivalent cationic and anionic charges on the same repeating unit. Over the past decade, such polymers have attracted considerable attention due to the outstanding anti-fouling properties attributed to their strong interaction with water via ionic solvation (in contrast to that of polyethylene glycol, which relies on hydrogen bonding to bind water), ease of functionalization, and design flexibility. Polycarboxybetaine, polysulfobetaine and poly(methacryloyloxyethyl phosphorylcholine) are three types of zwitterionic materials that have been most widely investigated. One of the major challenges for biomaterials is to maintain a controllable bio-interface, promote specific binding and resist non-specific binding of protein and cells, thus minimizing biofouling and potential infections. New biomaterials are urgently needed to address the intrinsic drawbacks such as poor mechanical property, degradability and biocompatibility.

Accordingly, there is a need for a hydrogel material that addresses or alleviates one or more disadvantages mentioned above. There is a need to provide a hydrogel material having desirable properties.

SUMMARY OF INVENTION

According to a first aspect, there is provided a polymeric composition comprising a plurality of metallic cross-linked monomers in the presence of a stabilizing agent, wherein said monomers are selected from (a) a carboxylic acryloyl monomer; (b) a sulfonic acryloyl monomer; (c) an amine acryloyl monomer; (d) a hydroxyl acryloyl monomer; (e) an alkyl acryloyl monomer; and (f) a polyalkylene hydroxyl acryloyl monomer.

Advantageously, the polymeric composition, when used on implanted materials, may have good anti-fouling property and biocompatibility to prolong the lifetime of implanted materials. The polymeric composition may have antimicrobial properties to eliminate infection and inflammation. The polymeric composition may have good mechanical property to avoid failure of the implanted material.

Advantageously, the use of the stabilizing agent such as a zwitterionic monomer may confer an overall charge neutrality to the polymeric composition since the zwitterionic monomer has both a positively charged moiety and a negatively charged moiety within the same side chain segment. As a result, the resultant polymeric composition has homogeneously distributed and balanced positive and negative charges, which may result in the anti-fouling property of the polymeric composition. This may lead to the polymeric composition having a high resistance against protein adsorption, bacteria adhesion and cell adhesion to thereby prevent biofouling.

Advantageously, the polymeric composition may be used as an anti-fouling hydrogel coating material. The polymeric composition, when used as an anti-fouling hydrogel coating material, may be safe, may elicit little inflammatory response in vivo, may resist capsule formation and/or may elicit minimal foreign body reaction in vivo. Furthermore, the polymeric composition when used as an anti-fouling hydrogel coating material, may have a longer in vivo lifetime as compared to conventional anti-fouling materials, may demonstrate very good resistance against non-specific protein adsorption, bacteria adhesion and cell adhesion, and display good biocompatibility in vitro, may be of soft elastic nature to be moulded into various shapes, may be of great transparency, may be of chemically defined (hence, not eliciting any immune response in a human or animal body), may be of low cost, and/or easier to prepare or operate.

According to another aspect, there is provided a method for forming a polymeric composition comprising a plurality of metallic cross-linked monomers in the presence of a stabilizing agent, wherein said monomers are selected from (a) a carboxylic acryloyl monomer; (b) a sulfonic acryloyl monomer; (c) an amine acryloyl monomer; (d) a hydroxyl acryloyl monomer; (e) an alkyl acryloyl monomer; and (f) a polyalkylene hydroxyl acryloyl monomer, wherein the method comprises the steps of (i) providing a solution mixture of the carboxylic acryloyl monomer, the sulfonic acryloyl monomer, the amine acryloyl monomer, the hydroxyl acryloyl monomer, the alkyl acryloyl monomer, the polyalkylene hydroxyl acryloyl monomer, the stabilizing agent and a source of a metallic cross-linker; and (ii) polymerizing said solution mixture with an acid initiator to thereby synthesize said polymeric composition.

Advantageously, the method may be carried out easily at room temperature.

According to another aspect, there is provided the use of the polymeric composition as defined herein as an anti-fouling hydrogel coating material on materials. The material may be biomedical materials.

Definitions

The following words and terms used herein shall have the meaning indicated:

The term 'polymeric composition' is to be interpreted broadly to include a network of polymer chains that entangle or cross-link with each other. The polymeric composition may include the use of cross-linkers to form the necessary chemical bonds between the various polymer chains.

Where the polymer composition is used as a hydrogel material or as a hydrogel, the polymer chains are usually hydrophilic. The polymeric composition may be made up of a (chemical) substance or mixture of substances to sometimes form as a colloidal gel with a degree of flexibility very similar to natural tissue in which water is the dispersion medium due to their significant water content. The hydrogel may be highly absorbent, containing over 90% water, and may be made up of natural or synthetic polymeric networks with different or similar functional properties. Hydrogels also possess an overall charge of poly-zwitterions that is neutral under normal conditions, notwithstanding that they are characterized by a high density of polymer-bound ion pairs attached to the polymer chain.

The term "alkyl group" is to be interpreted broadly to refer to straight chain or branched chain saturated aliphatic groups having from 1 to 16 carbon atoms, eg, 1, 2, 3, 4, 5, 6, 7, 8, 9, 10, 11, 12, 13, 14, 15 or 16 carbon atoms. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 5-methylheptyl, 1-methylheptyl, octyl, nonyl, decyl, undecyl, 2,2, 3-trimethyl-undecyl, dodecyl, 2,2-dimethyl-dodecyl, tridecyl, 2-methyl-tridecyl, 2-methyl-tridecyl, tetradecyl, 2-methyl-tetradecyl, pentadecyl, 2-methyl-pentadecyl, hexadecyl, 2-methyl-hexadecyl and the like.

The term "alkenyl group" is to be interpreted broadly to refer to straight or branched chain unsaturated aliphatic hydrocarbon groups having from 2 to 16 carbon atoms, eg, 2, 3, 4, 5, 6, 7, 8, 9, 10, 11, 12, 13, 14, 15 or 16 carbon atoms and having at least one double bond, of either E, Z, cis or trans stereochemistry where applicable, anywhere in the alkyl chain. Examples of alkenyl groups include but are not limited to ethenyl, vinyl, allyl, 1-methylvinyl, 1-propenyl, 2-propenyl, 2-methyl-1-propenyl, 2-methyl-1-propenyl, 1-butenyl, 2-butenyl, 3-butentyl, 1,3-butadienyl, 1-pentenyl, 2-pententyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, 1-heptenyl, 2-heptentyl, 3-heptenyl, 1-octenyl, trans-4-octenyl, trans-2-octenyl, 1-nonenyl, 1-decenyl, 1-undecenyl, 1-dodecenyl, 1-tridecenyl, 1-tetradecenyl, trans-7-tetradecenyl, 1-pentadecenyl, 1-hexadecenyl and the like.

The term "coating material" is to be interpreted broadly to refer to a covering material made up of a (chemical) substance or mixture of substances that forms a layer when applied to the surface of an object, usually referred to as the substrate. The purpose of applying the coating material may be decorative, functional, or both. The coating itself may be an all-over coating, completely covering the substrate, or it may only cover parts of the substrate.

The term "anti-fouling" as used herein refers to the ability of specifically designed materials and coatings to remove or prevent biofouling by any number of organisms on wetted surfaces or surfaces that are exposed to organisms. Since biofouling can occur almost anywhere water is present and poses risks to a wide variety of objects such as medical devices and membranes. The term "biofouling" thus refers to the accumulation of biological materials such as microorganisms, or proteins on surfaces that are exposed to such biological materials, whether in vivo or in vitro.

The terms "zwitterion" as used herein refers to a neutral molecule containing a positively charged ion at one end and a negatively charged ion at the other. (In some cases multiple positive and negative charges may be present.) Zwitterions have both ionic states simultaneously and are sometimes called inner salts. They are distinct from molecules that have dipoles at different locations within the molecule.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF OPTIONAL EMBODIMENTS

Exemplary, non-limiting embodiments of a polymeric composition will now be disclosed.

The polymeric composition comprises a plurality of metallic cross-linked monomers in the presence of a stabilizing agent, wherein said monomers are selected from (a) a carboxylic acryloyl monomer; (b) a sulfonic acryloyl monomer; (c) an amine acryloyl monomer; (d) a hydroxyl acryloyl monomer; (e) an alkyl acryloyl monomer; and (f) a polyalkylene hydroxyl acryloyl monomer.

The carboxylic acryloyl monomer may be a compound of formula I:

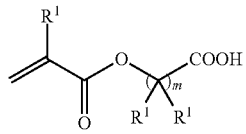

(I)

wherein m is an integer from 1 to 16, that is, 1, 2, 3, 4, 5, 6, 7, 8, 9, 10, 11, 12, 13, 14, 15 or 16; and $R^1$ is independently selected from the group consisting of hydrogen, alkyl and alkenyl.

The carboxylic acryloyl monomer of formula I may be

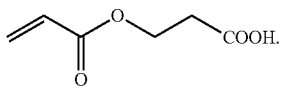

The sulfonic acryloyl monomer may be a compound of formula II:

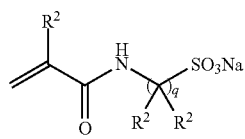

(II)

wherein q is an integer from 1 to 16, that is, 1, 2, 3, 4, 5, 6, 7, 8, 9, 10, 11, 12, 13, 14, 15 or 16; and $R^2$ is independently selected from the group consisting of hydrogen, alkyl and alkenyl.

The sulfonic acryloyl monomer of formula II may be

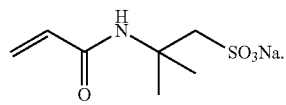

The amine acryloyl monomer may be a compound of formula III:

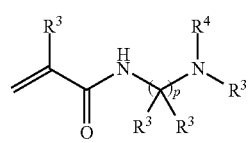

(III)

wherein p is an integer from 1 to 16, that is, 1, 2, 3, 4, 5, 6, 7, 8, 9, 10, 11, 12, 13, 14, 15 or 16;

$R^3$ is independently selected from the group consisting of hydrogen, alkyl and alkenyl; and $R^4$ is an alkyl.

The amine acryloyl monomer of formula III may be

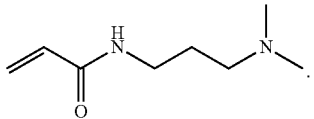

The hydroxyl acryloyl monomer may be a compound of formula IV:

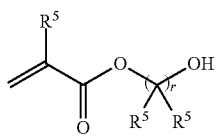

(IV)

wherein r is an integer from 1 to 16, that is, 1, 2, 3, 4, 5, 6, 7, 8, 9, 10, 11, 12, 13, 14, 15 or 16; and $R^5$ is independently selected from the group consisting of hydrogen, alkyl and alkenyl.

The hydroxyl acryloyl monomer of formula IV may be

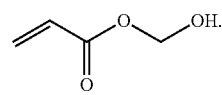

The alkyl acryloyl monomer may be a compound of formula V:

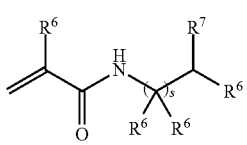

(V)

wherein s is an integer from 0 to 16, that is, 0, 1, 2, 3, 4, 5, 6, 7, 8, 9, 10, 11, 12, 13, 14, 15 or 16;

$R^6$ is independently selected from the group consisting of hydrogen, alkyl and alkenyl; and $R^7$ is an alkyl.

The alkyl acryloyl monomer of formula V may be

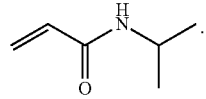

The polyalkylene hydroxyl acryloyl monomer may be a compound of formula VI:

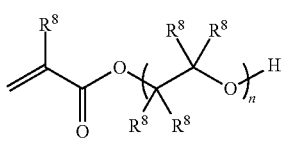

(VI)

wherein n is an integer from 1 to 100; and
R⁸ is independently selected from the group consisting of hydrogen, alkyl and alkenyl.

n may be an integer from the range of 1 to 100, 1 to 10, 10 to 100, 20 to 100, 30 to 100, 40 to 100, 50 to 100, 60 to 100, 70 to 100, 80 to 100, 90 to 100, 10 to 20, 10 to 30, 10 to 40, 10 to 50, 10 to 60, 10 to 70, 10 to 80, 10 to 90, 1 to 16 or 1 to 6.

The polyalkylene hydroxyl acryloyl monomer of formula VI may be

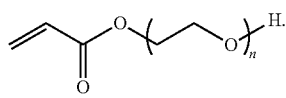

In the polymeric composition, all six of the above-mentioned acryloyl monomers having different functional groups are used. Hence, the different functional groups may be a carboxylic group, a sulfonic group, an amine group, a hydroxyl group, an alkyl group, and a polyalkylene hydroxyl group. Other monomers having other functional groups such as an amide group, a hydroxylalkyl group (such as 2-hydroxylethyl), a halide group (such as vinylidene fluoride) and/or a phosphoryl group (such as oxyethyl phosphorylcholine) can also be used.

The stabilizing agent of the polymeric composition may be a zwitterionic monomer. The stabilizing agent of the polymeric composition may be a protein-based acryloyl monomer. The protein-based acryloyl monomer may be a peptide-based acryloyl monomer. In an embodiment, the peptide-based acryloyl monomer may be an amino acid-based acryloyl monomer. The amino acid of the amino acid-based acryloyl monomer may be selected from the group consisting of a lysine, a glycine, a serine, a phenylalanine, a glutamic acid, an ornithine, an aspartic acid, a proline and a hydroxyproline groups.

Where the amino acid-based acryloyl monomer is lysine acryloyl monomer, the lysine may be selected from a L-lysine, a D-lysine or a L/D-lysine. The lysine acryloyl monomer may be methacryloyl-L-lysine (MLL) or

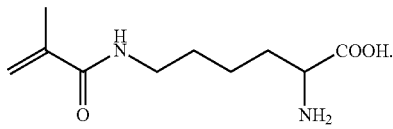

The concentration of the methacryloyl-L-lysine in the polymeric composition may dictate the mechanical properties of the hydrogel material such as rigidity, elasticity, transparency, bacteria and cell adhesion, cell viability, hemolysis and/or biocompatibility of the hydrogel material.

Where the stabilizing agent is a zwitterionic monomer with positive and negative charges on the same side chain segment, the monomer may result in either chemical or cross-link junctions within the polymeric composition. The chemically cross-linked networks have permanent junctions while physical networks have transient junctions that arise from either polymer chain entanglements or physical interactions such as ionic interactions, hydrogen bonds or hydrophobic interactions. The polymeric composition may comprise of ionic interactions between the various acryloyl monomers with different functional groups and the metallic cross-linker in the presence of a stabilizing agent.

The metallic cross-linker of the polymeric composition may be selected from an alkaline earth metal, an alkali metal or a transition metal. The metallic cross-linker of the polymeric composition may be alkaline earth metal and may be selected from Group 2 of the Periodic Table of Elements. The metallic cross-linker of the polymeric composition may be further selected from beryllium, magnesium, calcium, strontium, barium and radium.

As mentioned above, due to the use of a metallic cross-linker within the polymeric composition, a complex is formed with different acryloyl monomers of different functional groups, the metallic cross-linker and the stabilizing agent. The resultant polymeric composition would have a homogeneously distributed, balanced positively charged and negatively charged moieties within the polymeric composition, such that the overall charge neutrality is maintained throughout the polymeric composition. Advantageously, the homogeneous mixture of hydrophilic and balanced charged groups is shown to control anti-fouling properties. The homogeneous mixture of hydrophilic and balanced charged groups may be able to resist the microorganisms such as bacteria, proteins, cells and tissues.

The polymeric composition may have a metallic cross-linker that strengthens the mechanical properties of the hydrogel coating material. The polymeric composition may have the specific acryloyl monomers such as the hydroxyl-, alkyl- and polyalkylene hydroxyl-containing functional groups that facilitate the formation of hydrogel coating material with greater elasticity and transparency.

Advantageously, the polymeric composition, due to the presence of the stabilizing agent which is a zwitterionic monomer therein, may act as an anti-fouling hydrogel coating material when applied onto a biomedical material and be able to resist microorganisms when the coated biomedical material is exposed to the microorganisms. The homogeneously distributed positive and negative charges within the hydrophilic hydrogel material may be resistant to biological materials such as microorganisms (such as bacteria), proteins, cells and tissues and may not trigger a foreign body reaction or a minimal foreign body reaction when placed in vivo. The zwitteronic hydrogel material may show good biocompatibility in cell viability and hemolysis studies. The zwitteronic hydrogel material may demonstrate good resistance against protein adsorption, bacteria adhesion and cell adhesion. Due to the presence of the zwitteronic monomer, the anti-fouling hydrogel coating material may be stable and may last longer than conventional anti-fouling materials. Hence, the zwitterionic monomer aids 1) to control the absorption speed of organisms (such as bacteria, proteins, cells and tissues) from accumulating on the biomedical materials; and 2) to maintain the charge neutrality by retaining the positive and negative charges on the same side chain segment. This may be due to the formation of a thin layer of porous hydrogel material that is believed to form during the polymerization process, which slows down or retards the adsorption of microorganisms.

The polymeric composition may act as an anti-fouling hydrogel coating material or as a hydrogel. The anti-fouling hydrogel coating material may be coated on biomedical materials such as implants, devices and drug delivery systems. The hydrogel may be substantially transparent and allow some degree of light to pass through the hydrogel.

The polymeric composition may have a porous structure, wherein the porous structure allows transport of water, oxygen, essential minerals and nutrients. The pore size of the porous polymeric composition may be in the range of about 10 nm to about 700 nm, about 10 nm to about 100 nm, about 10 nm to about 200 nm, about 10 nm to about 300 nm, about 10 nm to about 400 nm, about 10 nm to about 500 nm, about 10 nm to about 600 nm, about 100 nm to about 700 nm, about 200 nm to about 700 nm, about 300 nm to about 700 nm, about 400 nm to about 700 nm, about 500 nm to about 700 nm, or about 600 nm to about 700 nm.

Exemplary, non-limiting embodiments of a method for forming a polymeric composition comprising a plurality of metallic cross-linked monomers in the presence of a stabilizing agent, wherein said monomers are selected from (a) a carboxylic acryloyl monomer; (b) a sulfonic acryloyl monomer; (c) an amine acryloyl monomer; (d) a hydroxyl acryloyl monomer; (e) an alkyl acryloyl monomer; and (f) a polyalkylene hydroxyl acryloyl monomer will now be disclosed.

The method comprises the steps of (i) providing a solution mixture of the carboxylic acryloyl monomer, the sulfonic acryloyl monomer, the amine acryloyl monomer, the hydroxyl acryloyl monomer, the alkyl acryloyl monomer, the polyalkylene hydroxyl acryloyl monomer, the stabilizing agent and a source of a metallic cross-linker; and (ii) polymerizing said solution mixture with an acid initiator to thereby synthesize the polymeric composition.

The method may be undertaken according to the following sequence:
  i. dissolving at least two acryloyl monomers in a source of a metallic cross-linker solution in solvent to obtain a metal-complex of cross-linking monomers;
  ii. mixing the remaining four acryloyl monomers together and adding this mixture to the metal-complex cross-linker solution;
  iii. adding a stabilizing agent which was dissolved in acid to the solution from (ii);
  iv. diluting the monomer solution from (iii) with the metallic cross-linker solution from (i) and used as a stock monomer solution;
  v. further diluting the stock monomer solution from (iv) with a solvent to a desired level; and
  vi. polymerizing the diluted solution from (v) with an acid initiator under ultraviolet light to thereby synthesize the polymeric composition.

Here, two acryloyl monomers may be dissolved in the metallic cross-linker solution in a suitable solvent (such as an aqueous solution) to form a solution of metal-complex of cross-linking monomers. The solution of metal-complex of cross-linking monomers may be mixed with the remaining four acryloyl monomers together. The stabilizing agent dissolved in acid may then be added to the six acryloyl monomers solution. The resultant solution may be diluted with the metallic cross-linker solution and used as a stock monomer solution. The stock monomer solution may be further diluted with solvent to a desired level. The stock monomer solution may be polymerized with the acid initiator under ultraviolet light to thereby synthesize the polymeric composition.

The method described above may provide a hydrogel with optimum rigidity, hardness and flexibility.

The solution of acryloyl monomers and metallic cross-linker may then be subjected to a temperature in the range of about 20° C. to about 40° C., about 25° C. to about 40° C., about 30° C. to about 40° C., about 35° C. to about 40° C., 20° C. to about 35° C., 20° C. to about 30° C. or about 20° C. to about 25° C., for a period of time ranging from about 10 to about 60 minutes, about 20 to about 60 minutes, about 30 to about 60 minutes, about 40 to about 60 minutes, about 50 to about 60 minutes, about 10 to about 50 minutes, about 10 to about 40 minutes, about 10 to about 30 minutes, or about 10 to about 20 minutes, to form the solution of metal-complex of cross-linking monomers. Subsequently, the solution of metal-complex of cross-linking monomers, four other acryloyl monomers and stabilizing agent dissolved in acid may then be subjected to a temperature and time period as stated above to form the solution of metal-complex of cross-linking monomers. The solution of metal-complex of cross-linking monomers is placed in a reactor and set at the temperature and time period as stated above.

The further diluted monomer solution may be polymerized using an acid initiator and be subjected to a temperature in the range of about 20° C. to about 40° C., about 25° C. to about 40° C., about 30° C. to about 40° C., about 35° C. to about 40° C., 20° C. to about 35° C., 20° C. to about 30° C. or 20° C. to about 25° C., under ultraviolet light for a period of time ranging from about 10 to about 60 minutes, about 20 to about 60 minutes, about 30 to about 60 minutes, about 40 to about 60 minutes, about 50 to about 60 minutes, about 10 to about 50 minutes, about 10 to about 40 minutes, about 10 to about 30 minutes, or about 10 to about 20 minutes, to form the polymeric composition.

The method described above may comprise of carboxylic and sulfonic acryloyl monomers at a ratio in the range of 1:10 to 10:1, 1:9 to 9:1, 1:8 to 8:1, 1:7 to 7:1, 1:6 to 6:1, 1:5 to 5:1, 1:4 to 4:1, 1:3 to 3:1, 1:2 to 2:1 or 1:1 to 1:1; amine and hydroxyl acryloyl monomers at a ratio in the range of 20:1 to 2:20, 19:1 to 2:19, 18:1 to 2:18, 17:1 to 2:17, 16:1 to 2:16, 15:1 to 2:15, 14:1 to 2:14, 13:1 to 2:13, 12:1 to 2:12, 11:1 to 2:11, 10:1 to 2:10, 9:1 to 2:9, 8:1 to 2:8, 7:1 to 2:7, 6:1 to 2:6, 5:1 to 2:5, 4:1 to 2:4, 3:1 to 2:3 or 2:1; and/or alkyl and polyalkylene hydroxyl acryloyl monomers at a ratio in the range of 1:10 to 10:1, 1:9 to 9:1, 1:8 to 8:1, 1:7 to 7:1, 1:6 to 6:1, 1:5 to 5:1, 1:4 to 4:1, 1:3 to 3:1, 1:2 to 2:1 or 1:1. In an embodiment, the six acryloyl monomers—carboxylic to sulfonic to amine to hydroxyl to alkyl to polyalkylene hydroxyl may be in a final ratio of 1:1:2:1:1:1 to form the polymeric composition.

The resultant polymeric composition may then be washed with deionized water to remove the monomers, cross-linking agent, the initiator, the soluble and extractable polymers and other impurities. The synthesis solvent may then be removed after formation of the gel by swelling the hydrogels in water. The washed hydrogel polymer may then be dried in air at a suitable temperature. The resultant hydrogel polymer may be easily collapsed after lyophilization.

The solution of metallic cross-linker is not particularly limited and depends on the type of metal that has the ability to cross-link the monomers efficiently. It is to be appreciated that a person skilled in the art would know the type of metallic cross-linkers that can cross-link the various monomers efficiently to form the desired metal-complex of cross-linking monomers. The metallic cross-linker may form a solution when dissolved in a suitable solvent. As the solvent used to dissolve the metallic cross-linker is generally water, the metallic cross-linker is generally soluble in water and a person skilled in the art would know what types of metallic cross-linker (based on the salts mentioned below) are soluble. Hence, the person skilled in the art would also not select a metallic cross-linker that is known to be insoluble for use in the present method.

The metallic cross-linker of the solution of metallic cross-linker may be derived from an alkaline earth metal salt selected from the group consisting of alkaline earth metal halide, alkaline earth metal nitrate, alkaline earth metal sulfate, alkaline earth metal citrate and alkaline earth metal oxalate.

The alkaline earth metal halide may be selected from the group consisting of alkaline earth metal chloride, alkaline earth metal bromide and alkaline earth metal iodide. In an embodiment, the alkaline earth metal of alkaline earth metal chloride may be selected from the group consisting of beryllium chloride, magnesium chloride, calcium chloride, strontium chloride, barium chloride and radium chloride. In a further embodiment, calcium chloride may be preferably used as such metallic cross-linker.

The alkaline earth metal nitrate may be selected from the group consisting of beryllium nitrate, magnesium nitrate, calcium nitrate, strontium nitrate, barium nitrate and radium nitrate.

The alkaline earth metal sulfate may be selected from the group consisting of beryllium sulfate, magnesium sulfate and calcium sulfate (low soluble).

The alkaline earth metal citrate may be selected from the group consisting of beryllium citrate (low soluble), magnesium citrate (low soluble) and calcium citrate.

The alkaline earth metal oxalate may be selected from the group consisting of beryllium oxalate and magnesium oxalate (low soluble).

The alkaline earth metal iodide may be selected from the group consisting of beryllium iodide, magnesium iodide, calcium iodide, strontium iodide and barium iodide.

The solution of acryloyl monomers and metallic cross-linker may be a solvent that is an organic solvent or an aqueous solvent. In an embodiment, water may be preferably used as such solvent.

The polymerization may be initiated thermally by ultraviolet-irradiation or by a redox initiator system. As mentioned above, the polymerization is first initiated by an acid initiator, followed by ultraviolet light for the time period as stated above. The acid initiator may be a photopolymerising initiator. The acid initiator may be an organic acid or an inorganic acid. In an embodiment, the organic acid may be a glutaric acid selected from the group consisting of a α-ketoglutaric acid (also known as oxoglutaric acid) and a β-ketoglutaric acid. Exemplary types of initiator may include but are not limited to, glutaric acid, potassium persulphate, poly(ethylene glycol), 1-hydroxycyclohexyl phenyl ketone, benzoin isobutyl ether or ammonium persulfate. In an embodiment, oxoglutaric acid may be preferably used as such initiator.

The concentration of the stabilizing agent dissolved in an acid may be in the range of about 0 to about 100 mol %, about 0 to about 10 mol %, about 10 mol % to about 100 mol %, about 20 mol % to about 100 mol %, about 30 mol % to about 100 mol %, about 40 mol % to about 100 mol %, about 50 mol % to about 100 mol %, about 60 mol % to about 100 mol %, about 70 mol % to about 100 mol %, about 80 mol % to about 100 mol %, about 90 mol % to about 100 mol %, about 10 mol % to about 90 mol %, about 10 mol % to about 80 mol %, about 10 mol % to about 70 mol %, about 10 mol % to about 60 mol %, about 10 mol % to about 50 mol %, about 10 mol % to about 40 mol %, about 10 mol % to about 30 mol % or about 10 mol % to about 20 mol %, before addition to the monomer solution.

The acid that the stabilizing agent is dissolved in may be an organic acid or an inorganic acid. Hydrochloric acid may be used as such acid for the stabilizing agent to be dissolved in.

It is to be noted that the above sequence provided is only exemplary and is not meant to limit the method to the exact sequence mentioned above. It is also possible to add in a number of acryloyl monomers to the source of metallic cross-linker solution which can range from two acryloyl monomers to all of the acryloyl monomers. The stabilizing agent can be added to this solution at the same time or at a later time as compared to the monomers.

Other applications of the polymeric composition will be discussed further below.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 1 shows the concentrations of the monomers and methacryloyl L-lysine (MLL) used in the synthesis of hydrogels A-J.

FIG. 2 is a series of Field Emission Scanning Electron Microscopy (FESEM) images of hydrogels A-J. Scale bar: 10 μm.

FIG. 3 shows the non-specific protein adsorption on hydrogels A-J and nitrocellulose membrane (positive control).

FIG. 4 demonstrates a *S. aureus* attachment on hydrogels A-J after 24 hours of culture. The bacteria were cultured on an uncoated petri dish as a control. Scale bar: 50 μm.

FIG. 5 shows an *E. coli* attachment on hydrogels A-J after 24 hours of culture. The bacteria were cultured on an uncoated petri dish as a control. Scale bar: 50 μm.

FIG. 6 demonstrates a fibroblasts attachment on hydrogels A-J after 24 hours of culture. The cells were cultured on an uncoated petri dish as a control. Scale bar: 100 μm.

FIG. 7 shows a viability of human primary fibroblast cultured for 24 hours in extracting medium used in incubating hydrogels A-J. The cells cultured in the absence of extracting medium were normalized as 100% viable.

FIG. 8 shows a hemolysis of rabbit red blood cells incubated with hydrogels A-J. In this assay, red blood cells treated with 0.2% Triton-X were used as a positive control, and red blood cells in PBS were used as a negative control.

FIG. 9 shows an image of hydrogel G after subcutaneous implantation in mice for two months.

FIG. 10 shows a histological analysis of tissues near hydrogel G that was subcutaneously implanted for two months. The tissues were stained with Hematoxylin and Eosin (H&E).

FIG. 11 shows the collagen formation in tissues near hydrogel G two months after subcutaneous implantation of hydrogel. The tissues were stained with Masson's trichrome.

EXAMPLES

Non-limiting examples of the invention will be further described in greater detail by reference to specific Examples, which should not be construed as in any way limiting the scope of the invention.

Materials

All chemical reagents were from Polysciences, Inc. (Warrington, Pa., U.S.A), Sigma-Aldrich Corp. (St. Louis, Mo., U.S.A.) and Merck KGaA (Darmstadt, Germany), and were used as received unless otherwise stated. *Staphylococcus aureus* (*S. aureus*; ATCC® No. 6538™) and *Escherichia coli* (*E. coli*; ATCC® No. 25922™) were purchased from American Type Culture Collection (ATCC; Manassas, Va., U.S.A.) and reconstituted according to standard protocols. Mueller-Hinton broth (MHB) was purchased from BD Diagnostics (Sparks, Md., U.S.A.) and used to prepare the microbial growth medium according to the manufacturer's instructions. Phosphate-buffered saline (PBS, 10×, pH=7.4) was purchased from 1st BASE (Singapore), and Luria broth containing 1.5% agar used for agar plate preparation was obtained from Media Preparation Unit (Biopolis Shared Facilities, A*STAR, Singapore).

Example 1

Hydrogel Preparation

Briefly, carboxylic monomer (1 mmol) and sulfonic monomer (1 mmol) were dissolved in 1 M $CaCl_2$ solution in de-ionized water to obtain the Ca-complex of cross-linking monomers. Subsequently, tert-amine monomer (2 mmol), hydroxyl-terminated monomer (1 mmol), isopropyl-terminated monomer 5 (1 mmol) and PEG monomer (1 mmol) were mixed and added to the Ca-complex cross-linker solution. The zwitterionic monomer, MLL, was dissolved in 1 N HCl at various concentrations (0-100 mol %), and added to the monomer solution. The monomer solution was further diluted with 1 M $CaCl_2$ solution, and used as a stock monomer solution. This monomer solution was further diluted with de-ionized water to the desired level, dependent on the optimal rigidity, hardness and flexibility of the gel achievable and polymerized using oxoglutaric acid initiator (10% solution in deionized water) under ultraviolet light for 30 minutes to obtain transparent hydrogels. The hydrogels obtained with different MLL concentrations were termed A-J (see FIG. 1).

Field Emission Scanning Electron Microscopy (FESEM)

FESEM analyses were performed with a field emission scanning electron microscopy (JEOL JSM-7400F) under an accelerating voltage of 4.0-6.0 keV. All the hydrogel samples were first polymerized using an initiator under ultraviolet light for 30 minutes to obtain transparent hydrogels. The morphologies of hydrogel were then examined with field emission scanning electron microscopy.

FIG. 2 shows the FESEM images of hydrogels A-J that incorporated lysine functionality in the material at various concentrations for systematic studies. FESEM studies showed that the materials have an interconnected porous structure (FIG. 2). Based on FIG. 1, FIG. 2A is hydrogel A with a 0% of MLL concentration. Similarly, FIG. 2B is hydrogel B with a 2.5% of MLL concentration, FIG. 2C is hydrogel C with a 5% of MLL concentration, FIG. 2D is hydrogel D with a 10% of MLL concentration, FIG. 2E is hydrogel E with a 20% of MLL concentration, FIG. 2F is hydrogel F with a 25% of MLL concentration, FIG. 2G is hydrogel G with a 30% of MLL concentration, FIG. 2H is hydrogel H with a 50% of MLL concentration, FIG. 2I is hydrogel I with a 75% of MLL concentration and FIG. 2J is hydrogel J with a 100% of MLL concentration. Based on the images, hydrogel G possessed larger pores, which collapsed after lyophilization.

Example 2

Protein Adsorption

Protein adsorption is commonly employed to determine if there are protein/protein footprints on the surface of a material. Since all proteins have positively and negatively charged residues randomly distributed on their surface, they can easily adhered to positively or negatively charged surfaces. Protein adsorption is associated with a biologically active material and is not desirable for an anti-fouling material.

To examine protein adsorption on the hydrogel surface, a commonly used model protein, bovine serum albumin (BSA), was employed. Typically, the BSA was dissolved separately in phosphate buffered saline (PBS) solution at a concentration of 100 μg/ml, and added to hydrogels that were formed in a 24-well plate. Nitrocellulose membrane was used as a positive control as it could adsorb a lot of proteins. The adsorption was allowed to proceed at 37° C. overnight. After incubation, the BSA solution was collected. The bicinhoninic acid (BCA) method was applied to quantify the amount of BSA by using Micro BCA. Protein assay reagent kit (Pierece, U.S.A.). The amount of BSA was calculated by measuring the absorbance at 562 nm. Assuming that the BSA that no longer remained in solution was adsorbed on the surface of the hydrogel, the percentage of BSA adsorption could be calculated using the following formula. Protein adsorption (%)=100−[(OD of BSA solution incubated with the hydrogel)/(BSA solution at a concentration of 100 μg/ml)×100], where OD=optical density at 562 nm. The mean value and standard deviation were calculated from 3 replicates for each sample.

FIG. 3 shows that the positive control, nitrocellulose membrane, adsorbed over 70% of the bovine serum albumin (BSA) on its surface after overnight incubation. In contrast, hydrogels A to J adsorbed less than 35% of the BSA on their surfaces. In particular, hydrogel G displayed excellent resistance to protein adsorption, showing less than 10% BSA adsorption.

Example 3

Bacteria Adhesion

Bacteria tend to adhere to the surfaces of medical devices. This poses a serious concern for infection as it may lead to the need to remove the implanted device.

*Staphylococcus aureus* (*S. aureus*) was selected for the bacteria adhesion study since it is a Gram-positive coccal bacterium frequently found on the skin. In addition, *Escherichia coli* (*E. coli*) were chosen for the bacteria adhesion study as it is a common Gram-negative bacterium. The bacteria concentration in Mueller Hinton Broth (MHB) was adjusted to an OD reading of 0.1 at a wavelength of 600 nm on a microplate reader (TECAN, Switzerland), which corresponded to ~$10^8$ CFU/mL. 500 μl of suspension of *E. coli* ($10^5$ CFU/mL) and *S. aureus* ($10^3$ CFU/mL) was added to the hydrogels formed in a 24-well plate. After incubation at 37° C. for 24 hours, the hydrogel surfaces were washed 3 times with PBS. To visualize the viable bacterial cells on the hydrogel surfaces, a LIVE/DEAD Baclight bacterial viability kit (Invitrogen) was used. Hydrogel was soaked in a dye solution at room temperature in the dark for 15 minutes. The stained bacteria were observed with fluorescence microscopy (Zeiss, Germany).

FIGS. 4 and 5 show that very few, if any *S. aureus* and *E. coli* bacteria, respectively, are adhered to the surfaces of hydrogels A to J after 24 hours of incubation. In contrast, a large number of bacteria were attached onto the petri dish (positive control). This demonstrated that the hydrogel materials were resistant to the adhesion of *S. aureus* and *E. coli*, which are among the most prevalent pathogens causing infections in the U.S. hospitals.

Example 4

Cell Adhesion

A good anti-fouling material should prevent cell adhesion, since cell adhesion would lead to foreign body reaction and cause an inflammatory response after implantation.

Human primary dermal fibroblasts (ATCC, PSC-201-010) were used in the cell adhesion study as they tend to adhere to surfaces easily, and can be cultured without substantial difficulty. Fibroblasts were cultured in Dulbecco's Modified Eagle Medium supplemented with 10% fetal bovine serum (FBS) and 2% penicillin streptomycin at 37° C. in a 5% $CO_2$ incubator. 500 μL of fibroblasts at $1 \times 10^5$ cells/ml were seeded on the surface of hydrogels in a 24-well plate. After 24 hours, the culture medium was replaced with the same amount of the extracting medium from the incubated hydrogels, and cultured for another 48 hours. Next, the attachment and morphology of the cells were assessed using Live/Dead Assay kit. The staining solution was prepared by adding 5 μL of Calcein stock solution (4 mM solution in dimethyl sulfoxide (DMSO)) and 20 μL of ethidium homodimer-1 (EthD-1) stock solution (2 mM solution in 1:4 DMSO/$H_2O$) to 10 ml of PBS solution in a dark environment. The staining solution was then added to the wells, and incubated at 37° C. in a 5% $CO_2$ incubator for 45 minutes. The stained cells were analyzed by fluorescence microscopy.

FIG. 6 shows that very few fibroblasts were adhered to hydrogels C, D and F, as compared to petri dish. All the adhered cells have normal morphology and were alive. The other 7 hydrogels did not appear to have any fibroblasts adhered to their surfaces, indicating their excellent resistance against cell adhesion.

Example 5

In Vitro Cytotoxicity a) Hemolysis Assay

It is important that an anti-fouling coating for implantable biomedical device does not cause hemolysis. To test for hemolysis, fresh rabbit blood was diluted to 4% (by volume) with PBS, and the diluted blood (100 μL) was placed on each hydrogel sample in a 96-well plate. 100 μL of PBS were then added to each well. To allow hemolysis to occur, the plate was incubated for 1 hour at 37° C. The 96-well plate was then centrifuged at 2200 rpm for 5 minutes. Aliquots of 100 μL of supernatant from each well were transferred to a new 96-well plate, and OD readings were recorded at a wavelength of 576 nm to assess hemoglobin release using the microplate reader (TECAN, Sweden). In this assay, red blood cells treated with 0.2% Triton-X were used as a positive control, and red blood cells in hydrogel-free PBS were used as a negative control. Percentage of hemolysis was calculated using the following formula. Hemolysis (%)=[(OD of sample−OD of negative control)/(OD of positive control−OD of negative control)]×100. The mean value and standard deviation were calculated from 3 replicates for each sample.

b) Cell Viability

To determine if the hydrogel materials were biocompatible, cytotoxicity of human primary dermal fibroblasts (HDFs) was examined. HDFs were purchased from ATCC (PSC-201-010), and cultivated using Dulbecco's Modified Eagle Medium supplemented with 10% FBS with 5% $CO_2$ and humidified atmosphere. The medium was changed every 2 days. The hydrogels were incubated in the culture medium at 37° C. for 24 hours to extract any soluble substances in the materials. HDFs were seeded in 96-well culture plates at $1 \times 10^4$ cells/well. After 24 hours, the culture medium was replaced with the same amount of the extracting medium from the incubated hydrogels. The cells were subsequently cultured for another 24 hours. The effect of materials on HDF cell viability was examined using 3-(4,5-dimethylthiazol-2-yl)-5-(3-carboxy-methoxyphenyl)-2-(4-sulfophenyl)-2H-tetrazolium (MTS) assay. MTS solution was added 12 h after cells were treated with the hydrogels. After 3 hours of incubation at 37° C. in 5% $CO_2$, the light absorbance was measured at a wavelength of 490 nm with a microplate reader. The cell viability was obtained as follows: (number of viable cells with hydrogel treatment)/(number of viable cells without hydrogel treatment). Experiments were conducted in triplicates for each sample.

c) Results

The cells proliferated well without showing any reduction in viability (FIG. 7). FIG. 8 shows that rabbit red blood cells remained healthy with <10% hemolysis in the presence of hydrogels. These two studies showed that hydrogels A-J were not toxic to HDFs and rabbit red blood cells.

Example 6

In Vivo Implantation a) Source of Mice

Adult C57BL/6 mice (8-week-old, 18-22 g) were used for animal studies. All mice eyes were examined for absence of ocular pathology before experiments were initiated. The experimental protocol was approved by the Institutional Animal Care and Use Committee of Biological Resource Centre, Agency for Science, Technology and Research (A*STAR), Singapore.

b) In Vivo Hydrogel Implantation

The hydrogel were implanted subcutaneously in mice for 1 week and 2 months. The mice were anesthetized by ketamine (150 mg/kg) and xylazine (10 mg/mL) via intraperitoneal injection (I.P.). A longitudinal incision (1 cm) was made on the central dorsal surface using surgical scissors to provide access to the subcutaneous space. Next, subcutaneous pockets were created with a blunt forceps for the implantation of hydrogel disks. The incision was closed with suture. The mice were sacrificed at 1 week and 2 months. The hydrogel and surrounding skin tissues were collected immediately, and prepared for histological analysis. The fixed samples were embedded in paraffin, sectioned and stained with hematoxylin and eosin (H&E) by the standard protocol. To investigate the collagen formation in tissues near the subcutaneously implanted hydrogel, the tissues were stained with Masson's trichrome.

c) Results

The new zwitterionic hydrogel materials demonstrated very good resistance against protein adsorption, bacteria adhesion and cell adhesion. They also show very good biocompatibility in the cell viability and hemolysis studies. In particular, hydrogel G provided excellent resistance against protein adsorption and was selected for further animal studies. It was implanted subcutaneously in C57BL/6 mice. FIG. 9 shows that hydrogel G was clear and transparent after 2 months of implantation. Representative H&E staining images revealed numerous cells found after 2 months of implantation (FIG. 10). These finding suggested that hydrogel G elicited very little inflammatory response after 2 months of implantation. This weak inflammatory reaction could be attributed to the hydrogel's resistance against non-specific protein adsorption, cell adhesion and bacteria adhesion. Masson's trichrome stain, which stains collagen blue, cytoplasm red and nuclei black, was used to examine capsule formation. After implantation of hydrogel G for 2 months, no collagen capsule formation was found surrounding the material (FIG. 11), indicating that hydrogel G did not elicit substantial foreign body reaction.

INDUSTRIAL APPLICABILITY

The polymeric composition may be used as an anti-fouling coating material and may be used in a variety of applications such as biomedical implants and devices, drug delivery systems, contact lenses and tissue scaffolds to protect the implants or devices from bacteria or cell adhesion, foreign body reaction and resist non-specific protein adsorption, thus minimizing biofouling and potential infections.

The polymeric composition may be applied as hydrogel or as an anti-fouling hydrogel coating material on biomedical materials to develop a hemocompatible non-fouling surface that may be flexible to contour according to a variety of biomaterials. The polymeric composition may comprise six acryloyl monomers comprising carboxylic, sulfonic and amine (such as tert-amine) groups, where the hydroxyl-, alkyl-(such as isopropyl-) and polyalkylene hydroxyl (PEG)-terminated monomers facilitate the formation of hydrogel with greater elasticity and transparency, and a stabiling agent (such as amino acid-terminated methacryloyl-L-lysine (MLL)) was used to enhance the zwitterionic property of the hydrogel. The polymeric composition may comprise a metal salt solution to provide a source of a metal as a cross-linker that forms a complex with the carboxylic and sulfonic groups to strengthen the mechanical properties. This polymer may be a porous material with great transparency and soft elastic nature that could be molded into various shapes, and excellent absorbent capability. The polymeric composition may demonstrate very good resistance against protein adsorption, bacteria adhesion and cell adhesion, and may display very good biocompatibility.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

What is claimed is:

1. A polymeric composition comprising a plurality of monomers in the presence of a stabilizing agent, wherein said monomers are selected from each of:
   a) an alkaline earth metallic cross-linked carboxylic acryloyl monomer;
   b) an alkaline earth metallic cross-linked sulfonic acryloyl monomer;
   c) an amine acryloyl monomer;
   d) a hydroxyl acryloyl monomer;
   e) an alkyl acryloyl monomer; and
   f) a polyalkylene hydroxyl acryloyl monomer, such that monomer a), monomer b), monomer c), monomer d), monomer e) and monomer f) are present in said polymeric composition.

2. The polymeric composition according to claim 1, wherein said carboxylic acryloyl monomer is a compound of formula I:

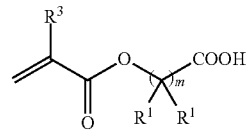

wherein m is an integer from 1 to 16; and $R^1$ is independently selected from the group consisting of hydrogen, alkyl and alkenyl.

3. The polymeric composition according to claim 1, wherein said sulfonic acryloyl monomer is a compound of formula II:

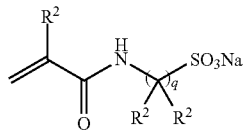

wherein q is an integer of 1 to 16; and $R^2$ is independently selected from the group consisting of hydrogen, alkyl and alkenyl.

4. The polymeric composition according to claim 1, wherein said amine acryloyl monomer is a compound of formula III:

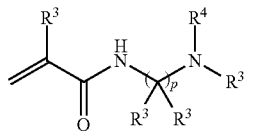

wherein p is an integer of 1 to 12;

$R^3$ is independently selected from the group consisting of hydrogen, alkyl and alkenyl; and $R^4$ is an alkyl.

5. The polymeric composition according to claim 1, wherein said hydroxyl acryloyl monomer is a compound of formula IV:

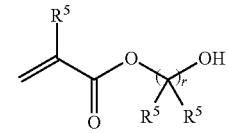

wherein r is an integer of 1 to 12; and $R^5$ is independently selected from the group consisting of hydrogen, alkyl and alkenyl.

6. The polymeric composition according to claim 1, wherein said alkyl acryloyl monomer is a compound of formula V:

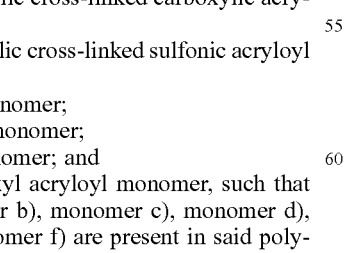

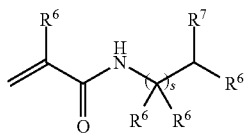

(V)

wherein s is an integer of 0 to 6;
$R^6$ is independently selected from the group consisting of hydrogen, alkyl and alkenyl; and
$R^7$ is alkyl.

7. The polymeric composition according to claim 1, wherein said polyalkylene hydroxyl acryloyl monomer is a compound of formula VI:

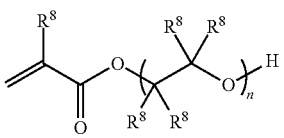

(VI)

wherein n is an integer of 2 to 100; and
$R^8$ is independently selected from the group consisting of hydrogen, alkyl and alkenyl.

8. The polymeric composition according to claim 1, wherein said stabilizing agent is a zwitterionic monomer.

9. The polymeric composition according to claim 8, wherein said zwitterionic monomer is a protein-based acryloyl monomer.

10. The polymeric composition according to claim 9, wherein said protein-based acryloyl monomer is a peptide-based acryloyl monomer.

11. The polymeric composition according to claim 10, wherein said peptide-based acryloyl monomer is an amino acid-based acryloyl monomer.

12. The polymeric composition according to claim 11, wherein the amino acid of said amino acid-based acryloyl monomer is selected from the group consisting of a L-lysine, a D-lysine, a L/D-lysine, a glycine, a serine, a phenylalanine, a glutamic acid, an ornithine, an aspartic acid, a proline and a hydroxyproline groups.

13. The polymeric composition according to claim 1, wherein said alkaline earth metal is selected from the group consisting of beryllium, magnesium, calcium, strontium, barium and radium.

14. The polymeric composition according to claim 1, wherein said polymeric composition is a hydrogel coating material.

15. A method for forming a polymeric composition comprising a plurality of monomers in the presence of a stabilizing agent, wherein said monomers are selected from each of:
   a) an alkaline earth metallic cross-linked carboxylic acryloyl monomer;
   b) an alkaline earth metallic cross-linked sulfonic acryloyl monomer;
   c) an amine acryloyl monomer;
   d) a hydroxyl acryloyl monomer;
   e) an alkyl acryloyl monomer; and
   f) a polyalkylene hydroxyl acryloyl monomer, such that monomer a), monomer b), monomer c), monomer d), monomer e) and monomer f) are present in said polymeric composition,
wherein the method comprises the steps of:
   i) providing a solution mixture of the alkaline earth metallic cross-linked carboxylic acryloyl monomer, the alkaline earth metallic cross-linked sulfonic acryloyl monomer, the amine acryloyl monomer, the hydroxyl acryloyl monomer, the alkyl acryloyl monomer, the polyalkylene hydroxyl acryloyl monomer, the stabilizing agent and a source of an alkaline earth metallic cross-linker; and
   ii) polymerizing said solution mixture with an acid initiator to thereby synthesize said polymeric composition.

16. The method according to claim 15, wherein said metallic cross-linker source is an alkaline earth metal salt selected from the group consisting of beryllium chloride, magnesium chloride, calcium chloride, strontium chloride, barium chloride, radium chloride, alkaline earth metal bromide, alkaline earth metal iodide, alkaline earth metal nitrate, alkaline earth metal sulfate, alkaline earth metal citrate and alkaline earth metal oxalate.

17. The method according to claim 15, wherein said acid initiator is a glutaric acid selected from the group consisting of α-ketoglutaric acid and β-ketoglutaric acid or an inorganic acid.

18. The method according to claim 15, wherein said solution mixture is provided in a solvent selected from an organic solvent or an aqueous solvent.

19. The method according to claim 15, further comprising the step of providing said stabilizing agent at a concentration in the range of 0 to 100 mol % to said solution mixture.

20. The method according to claim 15, wherein said polymerizing step is undertaken for a period of time in the range of 10 minutes to 60 minutes.

* * * * *